United States Patent [19]

Mochow

[11] 4,438,845
[45] Mar. 27, 1984

[54] CONTROL PACKAGE FOR ELONGATED ARTICLE

[76] Inventor: Charles M. Mochow, Rte. #1, Iron Hill, Burns, Tenn. 37209

[21] Appl. No.: 514,553

[22] Filed: Jul. 18, 1983

[51] Int. Cl.³ .............................................. B65D 83/10
[52] U.S. Cl. ..................................... 206/366; 206/443; 229/15
[58] Field of Search ............... 206/366, 365, 364, 443, 206/820; 229/15

[56] References Cited

U.S. PATENT DOCUMENTS

| | | | |
|---|---|---|---|
| 3,207,302 | 9/1965 | Hobbs | 206/366 |
| 4,121,755 | 10/1978 | Meseke et al. | 206/366 |
| 4,142,633 | 3/1979 | Raghavachari | 206/366 |
| 4,333,567 | 6/1982 | Leonard | 206/366 |

*Primary Examiner*—Joseph Man-Fu Moy
*Attorney, Agent, or Firm*—Harrington A. Lackey

[57] ABSTRACT

A package for an elongated product, such as a syringe, including an elongated platform and means retaining the elongated product co-extensively on top of the platform. The platform forms a top wall for a lower container defining a discard chamber having closed side, bottom and end walls. An elongated opening formed in the platform member above the discard chamber includes opposed side edge portions defining elastic closure members occupying a normal closed position over the discard chamber, and a depressed open position when a discarded product or syringe is forced downward against the closure members to open the elongated opening and permit the syringe to pass from the platform chamber member downward through the opening into the discard chamber.

The package is further characterized by having laterally disposed flanges for detachable connection to adjacent flanges or to opposed flanges of adjacent containers to provide a multiple product package in which individual packaged products may be separated from the multiple package as needed.

The multiple packages are also especially constructed and configured to permit nesting.

9 Claims, 6 Drawing Figures

CONTROL PACKAGE FOR ELONGATED ARTICLE

BACKGROUND OF THE INVENTION

This invention relates to a control package for elongated articles, and more particularly to a control package for syringes.

Typically, syringes are provided with caps or sheathes to cover and protect the needle of the syringe from exposure to inadvertent puncture of persons or objects. In the preferred use of the syringe, the cap or sheath is maintained over the needle until the needle is to be introduced into the patient's vein, for withdrawal of blood, or for introduction of various solutions into the patient. Furthermore, after the syringe is used, the cap or sheath should be re-applied over the needle to prevent inadvertent puncture by the exposed syringe needle, and then the syringe is disposed of, preferably by incineration.

There are various ways of packaging syringes for distribution and storage, and various containers for the syringes, but none of these packages or containers are provided with a particular type of means for controlling the disposition of the syringes, particularly after use.

Because of this absence of adequate control over the disposition of syringes, there is a high incidence of accidents to hospital personnel and to patients caused by the puncture of the persons by the needles of used syringes which have been mislaid, lost or forgotten. These inadvertent punctures by used syringe needles have caused numerous cases of hepatitis, some of which have been quite serious.

Hospital records have shown that in many instances, onethird of all accidents to nurses on duty in hospitals have been caused by needle punctures of used syringes. In addition to nurses, other hospital personnel, as well as patients, have been accidentally punctured by the needles of used syringes. Used syringes forgotten on a table or tray, have accidentally punctured a misplaced hand, finger, or arm. Used syringes lost in the bed clothing have accidentally punctured patients and laundry personnel. Careless handling or wielding of a syringe after use has punctured the operator of the syringe or other personnel in the vicinity.

After a syringe is used, the removed cap is rarely reapplied to the syringe to cover the needle, but is either lost, ignored, or intentionally discarded.

The following U.S. patents disclose various types of packages or retainer means for various types of syringes or phials, side-by-side:

| | | |
|---|---|---|
| 2,598,492 | Boes | May 27, 1952 |
| 2,887,215 | Hutchison | May 19, 1959 |
| 4,149,635 | Stevens | Apr. 17, 1979 |

The Glass U.S. Pat. No. 2,339,555 discloses a packing case including individual containers having means for holding elongated objects, such as spark plugs, in each of the compartments which are severably joined together in a multiple article package. The package disclosed in the Glass patent also includes transparent sheet material for covering the packages.

The Thies et al U.S. Pat. No. 3,226,607 discloses a disposable carton having a trap door in the form of a collapsible, foldable or pivotal flap permitting entrance of a used syringe into the carton.

The Heppler U.S. Pat. No. 4,349,338 discloses a housing for receiving a plurality of syringes in independent adjacent chambers or compartments, and a removable drawer at the bottom of the housing for containing used syringes.

SUMMARY OF THE INVENTION

It is an object of this invention to provide a package particularly adapted to contain one or more sterile syringes for display and storage, each package including a separate chamber or compartment for receiving the used syringe in a protected manner.

Furthermore, the package made in accordance with this invention is particularly adapted to facilitate a controlled distribution and return of the syringes, and to include the accountability for used and unused syringes.

In a preferred form of the invention, the package includes multiple units detachably connected side-by-side, so that each package unit can be separated and distributed, and/or each syringe may be separated from its package unit and used or distributed.

Each package unit includes an elongated, preferably rectangular platform upon which the unused sterile syringe is supported and retained in a position of display, and preferably covered with a transparent sheet so that each package unit may be immediately identified as either containing or not containing a syringe. Each package unit also includes an elongated discard container having closed bottom and side walls and an upper portion sealed or secured to the bottom of the platform member. Each of these discard chambers is adapted to receive a used syringe. An elongated opening is formed along the longitudinal center line of the platform member in registry with the discard chamber. Flexible elastic closure members are formed along the opposed edges of the opening to permit a syringe to be supported upon the platform member and the closure members in the original package position. The elasticity of the closure flaps or members permits them to yield downward under the pressure of a used syringe forced downward through the opening past the enclosure flaps from the platform member into the discard chamber. After the used syringe is fully received in the discard chamber, the elastic flaps immediately return to their closed position to prevent the used syringe from being released from the discard chamber.

After the package units, including the used syringes in their discard chambers, have been accounted for, these used packages may be disposed of, or preferably destroyed.

The multiple package units are preferably constructed so that their container side walls taper downward and are spaced from the corresponding side walls of adjacent packages to permit multiple packages to be nested upon each other.

If the head nurse at a hospital station is issued a multiple syringe package including, for example, 6 package units, each package unit retaining an unused syringe, the head nurse can separate each package unit from the remaining units, as needed, and issue them to a nurse for use on a patient. At the same time, the head nurse will make a note on a record chart showing that particular syringe on the chart and the nurse to whom the package unit is issued. The nurse then has in her possession, the package unit including the unused syringe in its original package form, and the discard chamber. After the cover is separated from the platform, the syringe is removed, the needle cap is removed and the syringe used. Preferably the cap is then restored to cover the used needle, but even if it is not, the entire used syringe is forced down through the opening in the platform of the package unit until it is received entirely within the discard chamber. Thus, the used syringe is completely isolated from any persons. The nurse then returns the uncovered package, with the used syringe in the discard chamber, to the head nurse, who indicates the return of the syringe package and arranges for the disposal of, or destruction of, the used syringes which are returned to her over a period of time, such as a day.

Although this system is subject to human error, it is believed with the proper instruction, accustomed usage, and the fact that the individual nurse has within her possession or control, not only the syringe before and after it is used, but also the syringe package unit including its own discard chamber, accidents from used syringes will be substantially decreased.

The package unit has a distinct advantage in its self-closing, elastic flaps along the opening in the platform to the discard chamber, which yield to the force of the downwardly thrust used syringe. No extra effort is required on the part of the syringe operator to first open a flap, door or closure to the discard chamber and then re-close the closure in order to prevent the used syringe from falling out of the discard chamber.

DESCRIPTION OF THE PREFERRED EMBODIMENT

Figure 1:
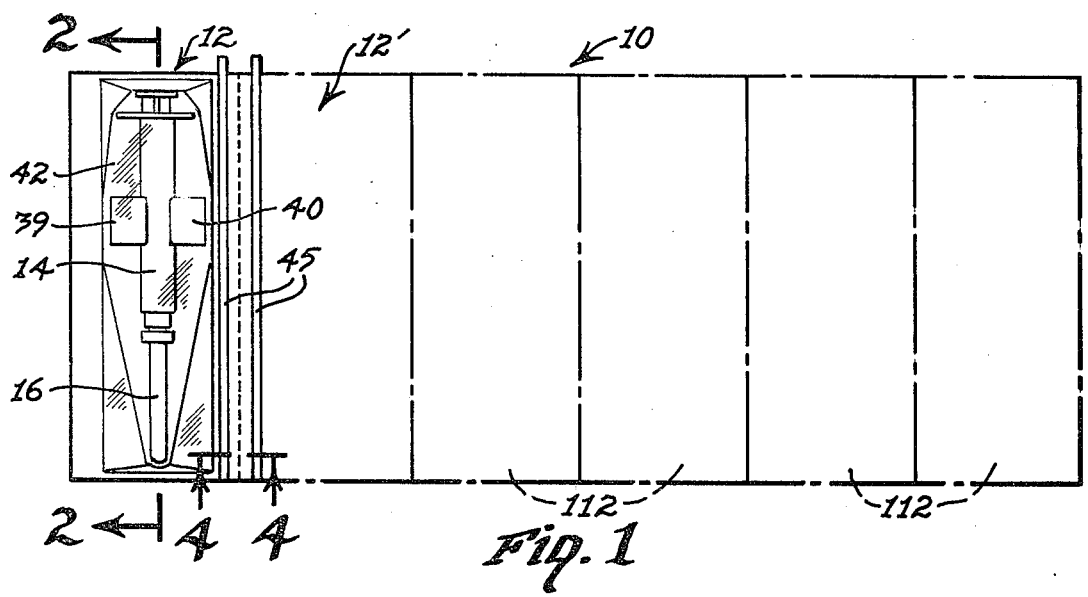
FIG. 1 is a top plan view of a package unit made in accordance with this invention, containing an unused sterile syringe in packaged position, and illustrating five additional package units in phantom, detachably connected side-by-side to form a multiple product package.

Referring now to the drawings in more detail, FIG. 1 discloses a multiple package 10 including specifically six package units 12, 12' and 112, detachably connected side-by-side parallel to each other. Each of the package units 12, 12' and 112 are identical to each other in size, shape and construction, and each of the package units is adapted to receive an elongated article or product, such as a barrel syringe 14 having a needle 15, and a needle sheath or cap 16.

The package unit 12 includes an elongated, preferably rectangular, planar platform member 18 of a length slightly greater than the length of a syringe 14, and of substantially greater width.

Secured to, and preferably sealed to, the bottom of the platform member 18 is an elongated container 20 having a bottom wall 21, side walls 22 and 23 and end walls 24 and 25. The upper portion of the container 20 preferably includes a pair of longitudinally extending flanges 26 and 27 projecting transversely outward from the upper edges of the side walls 22 and 23 to fit flush against the bottom surface of the platform member 18. The flanges 26 and 27 may be heat-sealed, fused or secured by adhesives to the abutting faces of the platform member 18, if desired. Thus, the bottom wall 21, the side walls 22 and 23, the end walls 24 and 25 and the platform member 18 form or define an enclosed elongated discard chamber 28. The discard chamber 28 must be at least as long as the used syringe 30 (FIG. 2), as well as having a depth and width sufficient to accommodate and receive the used syringe 30.

In order to gain access to the discard chamber 28, an elongated opening 32 is formed longitudinally, preferably along the mid-line, of the platform member 18. The opposed edges 33 of the elongated opening 32 define a plurality of opposed closure members, such as the elastic flaps 35 (FIG. 5).

The entire platform member 18 may be made of a thin monolithic plastic material having the desired elasticity for the closure members 35. The closure members 35, as disclosed in the drawings, are part of the platform member 18 formed by cutting the opening 32 of the desired shape. As disclosed in FIG. 5, the edges 33 have been formed of a saw-toothed shape by zig-zag cuts through the platform member 18 on opposite sides of the opening 32. Moreover, the edges 33 are formed in such a manner that the opposed projecting portions of the edges 33 form opposed triangular-shaped closure members or flaps 35. Furthermore, as disclosed in FIG. 5, each flap 35 may bend about a hinge line, such as the dashed hinge lines 36.

Figure 3:
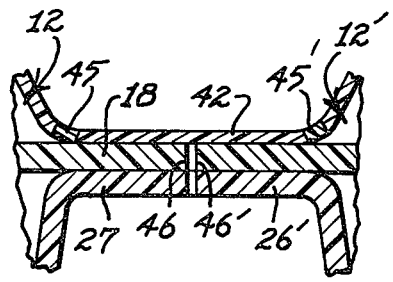
FIG. 3 is a section taken along the line 3—3 of FIG. 2.
Figure 2:
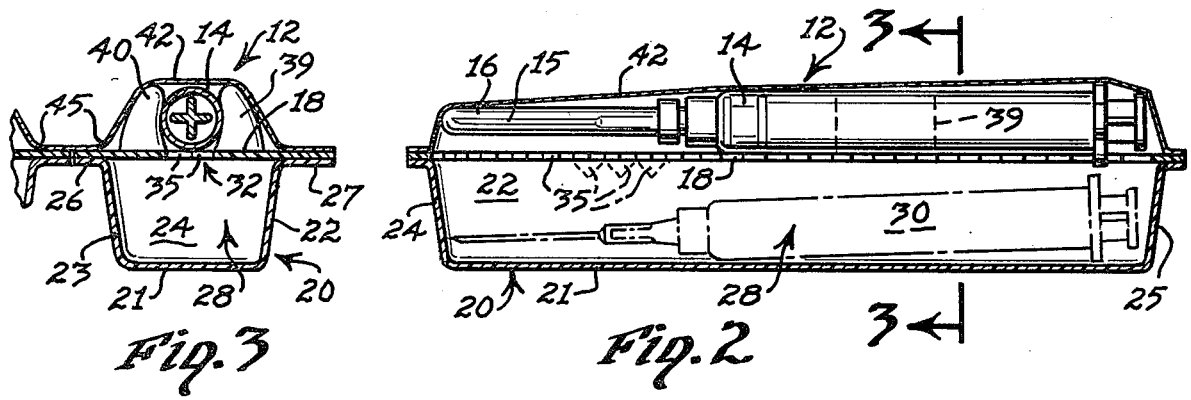
FIG. 2 is an enlarged section taken along the line 2—2 of FIG. 1, and illustrating a used syringe in phantom within the discard chamber.

The elastic flaps 35 normally lie in the same plane as the platform member 18 in a closed position to prevent entry or exit of the syringe 14 through the opening 32, and also to provide support for the syringe 14 in its packaged position as disclosed in solid lines in FIGS. 1, 2 and 3. As disclosed in the drawings, the syringe 14 is normally retained in its displayed position to extend longitudinally and centrally of the elongated opening 32.

Figure 5:
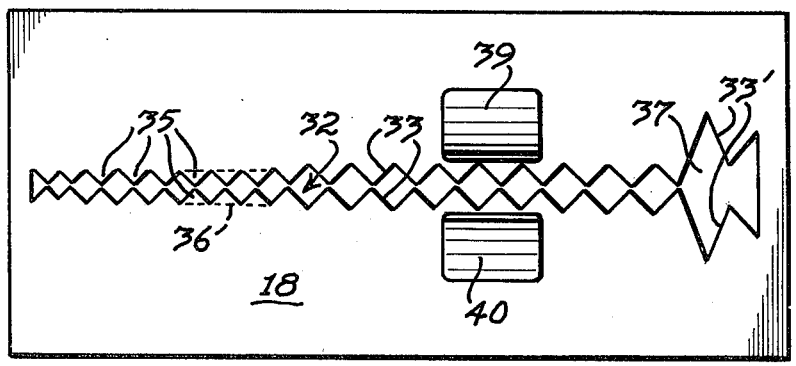
FIG. 5 is an enlarged top plan view of a package unit made in accordance with this invention, with the cover and syringe removed.

As disclosed in FIG. 5, the edges 33' have a slightly different configuration to provide a larger opening portion 37 to permit entry of the larger head portion of the syringe 14 through the opening 32.

The sizes of the opening 32 and the flaps 35 are such that when the syringe 14 is forced down through the opening 32, the flaps 35 will be biased downward and away from each other to permit the syringe 14 to pass from a position above the platform member 18 down into the discard chamber 28. When the used syringe 30 has been deposited on the bottom of the chamber 28, the elasticity of the flaps 35 will cause them to return to their original substantially co-planar positions as disclosed in FIGS. 2, 3 and 5.

It will be understood that the elastic flaps 35, may be of different configuration and different arrangement to accommodate elongated syringes or other articles of different shapes, so long as the above functions of opening and closing access to the opening 32 are retained.

In order to hold the syringe 14 in its packaged position, as disclosed in FIGS. 1-3, a pair of elastic clamp elements or jaws 39 and 40 are preferably integrally formed in the top surface of the platform member 18 to project above the surface of the platform member 18 on opposite sides of the opening 32 as disclosed in FIGS. 1, 3 and 5. The clamp jaws 39 and 40 may be of any configuration, so long as they snugly engage opposite sides of the barrel of the syringe 14 to hold the syringe 14 in its normal packaged position during shipment and storage, yet permit the syringe 14 to be manually removed from the platform member 18. The jaws 39 and 40 may have a snap-action in engaging and releasing the syringe 14.

Preferably a transparent plastic cover member 42, which may be flexible or rigid, is shaped to extend over the top of the platform member 18, the jaws 39 and 40 and the syringe 14 in its packaged position, as disclosed in FIGS. 2 and 3. If the unit cover 42 is of flexible sheet material, it may be laid in a single sheet from the edge of one package unit 12 across all of the 6 package units 12' and 112 to the opposite free edge of the last package unit 112. The intermediate portions of the plastic sheet material may be heat-sealed to the corresponding adjacent edges of the platform members 18, in order to compartmentalize each package unit and separate each displayed syringe 14 from any other syringe in any other package unit.

If desired, the covers 42 may be vacuum-molded into predetermined hollow shapes in a fixed configuration and secured by heat sealing or light adhesive to each of the corresponding package units 12.

It is important that the cover members 42 be transparent in order to determine if any particular platform member is supporting an unused syringe 14, in order to maintain control and accountability of the syringes.

Figure 4:
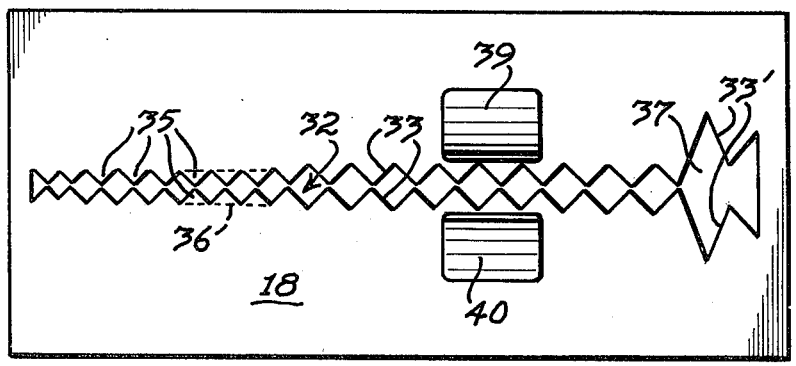
FIG. 4 is an greatly enlarged fragmentary section taken along the line 4—4 of FIG. 1.

FIG. 4 illustrates the junction between a pair of opposed edges of flanges 27 and 26' of adjacent package units 12 and 12'. Portions of the flexible sheet cover member 42 may be segmented to form peelable tape strips 45 and 45'. The portion of the cover member 42 between the tape strip 45 and 45' is secured to the top surfaces of the adjacent portions of the platform members 18 by heat-sealing or other adhesive means. The opposing edges 46 and 46' of the adjacent portions of the platform members 18 and adjacent flanges 27 and 26' are preferably formed of perforated or scored lines in continuous sheet material.

When it is desired to separate an individual package unit, such as the package unit 12 from the package unit 12', the unit 12 is pulled from the unit 12' to cause the units to separate along the perforated edges 46 and 46', simultaneously tearing the cover member 42 along the same longitudinal plane. It will be understood that other types of means may be employed for detachably connecting adjacent package units 12 and 12' and 112, such as weakened lines or reduced thicknesses of plastic or paper sheet material, and such detachable connection structures form no part of the invention per se.

When it is desired to remove a sterile syringe 14 from its package unit 12, the tape strip 45 is pulled to separate the cover member 42 from the corresponding unit.

It will be noted that separation of one package unit 12 from its adjacent package unit 12' will leave the cover members 42 completely sealing the respective syringes even though the cover member sheet has been ruptured along the separated edges 46 and 46'.

In the use of a multiple package 10, made in accordance with this invention, the six package units 12, 12' and 112 are identified and recorded, for example, at a nursing station in a hospital by the head nurse. When a syringe is needed by a nurse, the head nurse separates the package unit 12 from the package unit 12', records the name of the nurse and the identification of the package unit 12 and gives the package unit 12 to the nurse. The nurse will then take the package unit 12 to the area of the hospital where the syringe unit is to be used. The cover 42 is removed from the package unit 12 by pulling the tape strip 45, and the syringe 14 is pulled and released from between the jaws 39 and 40. The package unit 12 is then placed in a desired location for re-use. The cap 16 is removed, the syringe used upon the patient, and preferably the cap 16 is replaced over the exposed needle 15.

Whether the cap 16 is replaced or not, the nurse places the used syringe 30 upon the top of the platform member 18, in alignment with and over the elongated opening 32. The used syringe 30 is then forced downward through the opening 32 causing the elastic flaps 35 to flex downward separating from each other and enlarging the opening 32 to permit the used syringe 30 to pass through the opening 32 and down into the discard chamber 28. After the used syringe 30 has been deposited in the discard chamber 38, the elasticity of the closure flaps 35, causes the flaps 35 to return to their original planar closed position to trap the used syringe 30 within the discard chamber 28. The package 12 containing the used syringe 30 is then returned to the head nurse where the return of the used syringe 30 is recorded. The used trapped syringe 30 and its package 12 is retained for ultimate disposition, and preferably destruction.

Figure 6:
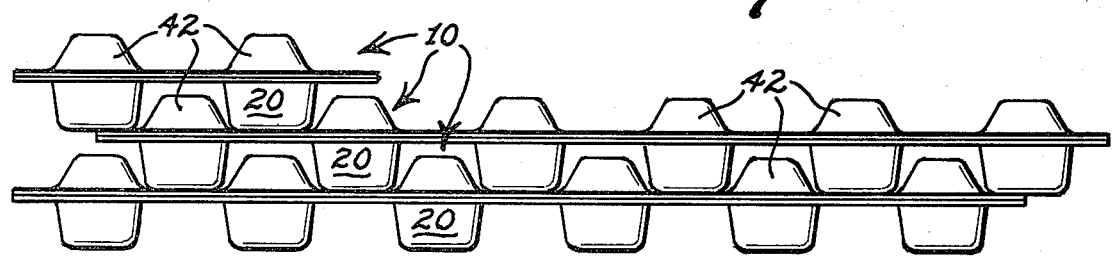
FIG. 6 is an end elevation of several stacked and nested multiple product packages made in accordance with this invention.

As best disclosed in FIGS. 3 and 6, the side walls 22 and 23 of each package unit preferably converge downward slightly. Moreover, adjacent walls 22 and 23 of adjacent package units 12, 12' and 112 are spaced apart sufficiently that several packages 10 may be stacked in a staggered relationship to permit nesting of the containers 20 between the covers 42 of subjacent multiple packages 10.

What is claimed is:

1. A package for an elongated product having a predetermined length and transverse dimension, comprising:
    (a) an elongated container having closed side and bottom walls and an upper portion, defining a discard chamber having a length, width and depth greater than the corresponding dimensions of a discarded elongated product received within said discard chamber,
    (b) an elongated platform member covering the upper portion of said discard chamber, said platform member being of a sufficient length and width for receiving an elongated product on top of said platform member and above said discard chamber, in a packaged position,
    (c) an elongated opening formed through, and extending longitudinally of, said platform member,
    (d) said elongated opening having opposed edge portions defining elastic closure members normally occupying a closed position in which the spacing between at least some of the opposed edge portions is less than the transverse dimension of the elongated product in said package position, and said closure members being adapted to support said elongated product in said packaged position,
    (e) said closure members being yieldable to the downward pressure of an elongated discarded product having a length less than the length of said opening when said product is forced downward from said platform member into said discard chamber, and
    (f) means retaining an elongated product in said packaged position on said platform member.

2. The invention according to claim 1 in which said opposed edge portions are undulating longitudinally of said opening.

3. The invention according to claim 2 in which said opposed edge portions comprise serrated closure members.

4. The invention according to claim 3 in which the inward projection portions of said serrated closure members oppose each other.

5. The invention according to claim 4 in which the depth of said container and the transverse dimensions of said serrated closure members are such that said closure members in said downward yielding positions clear a discarded product received in said discard chamber to permit said closure members to return to said closed position.

6. The invention according to claim 1 in which said retaining means comprises opposed elastic clamp members projecting upward from said platform member on opposite sides of said elongated opening for detachably receiving and holding a product in said packaged position.

7. The invention according to claim 1 in which the upper portions of said containers have transversely outward projecting flanges, and means detachably securing opposing flanges of adjacent containers to provdie a multiple container package having parallel containers.

8. The invention according to claim 7 further comprising transparent cover members extending over each of said platforms for covering a product on each platform in said packaged position.

9. The invention according to claim 8 in which the side walls of each container converge downward, and opposed side walls of adjacent containers are spaced apart sufficiently to permit nesting of one multiple container package upon another multiple container package.

* * * * *